(12) United States Patent
Pigazzi et al.

(10) Patent No.: US 12,319,678 B2
(45) Date of Patent: Jun. 3, 2025

(54) THIORIDAZINE DERIVATIVES AND THEIR USE FOR THE TREATMENT OF CANCER

(71) Applicants: UNIVERSITA' DEGLI STUDI DI PADOVA, Padua (IT); ISTITUTO DI RICERCA PEDIATRICA CITTÀ DELLA SPERANZA, Padua (IT)

(72) Inventors: Martina Pigazzi, Padua (IT); Claudia Tregnago, Albignasego (IT); Romeo Romagnoli, Ferrara (IT)

(73) Assignees: UNIVERSITA' DEGLI STUDI DI PADOVA, Padua (IT); ISTITUTO DI RICERCA PEDIATRICA CITTÀ DELLA SPERANZA, Padua (IT)

( * ) Notice: Subject to any disclaimer, the term of this patent is extended or adjusted under 35 U.S.C. 154(b) by 750 days.

(21) Appl. No.: 17/640,362

(22) PCT Filed: Sep. 3, 2020

(86) PCT No.: PCT/EP2020/074529
§ 371 (c)(1),
(2) Date: Mar. 4, 2022

(87) PCT Pub. No.: WO2021/043862
PCT Pub. Date: Mar. 11, 2021

(65) Prior Publication Data
US 2022/0340554 A1     Oct. 27, 2022

(30) Foreign Application Priority Data

Sep. 6, 2019  (IT) .................. 102019000015809

(51) Int. Cl.
*C07D 417/06* (2006.01)
*A61P 35/02* (2006.01)

(52) U.S. Cl.
CPC ............ *C07D 417/06* (2013.01); *A61P 35/02* (2018.01)

(58) Field of Classification Search
CPC ......... C07D 417/06; A61P 35/00; A61P 35/02
See application file for complete search history.

(56) References Cited

FOREIGN PATENT DOCUMENTS

CN          104829554 A       8/2015

OTHER PUBLICATIONS

Balgobind et al. "Novel prognostic subgroups in childhood 11q23/MLL-rearranged acute myeloid leukemia: results of an international retrospective study." Blood, The Journal of the American Society of Hematology 114.12 (2009): 2489-2496.

Bisio et al. "NUP98-fusion transcripts characterize different biological entities within acute myeloid leukemia: a report from the AIEOP-AML group." Leukemia 31.4 (2017): 974-977.
Blume et al. "Stepping test in mice: a reliable approach in determining forelimb akinesia in MPTP-induced Parkinsonism." Experimental neurology 219.1 (2009): 208-211.
Duque-Afonso et al. "The AML salad bowl." Cancer Cell 25.3 (2014): 265-267.
Eising et al. "Vinylboronic acids as fast reacting, synthetically accessible, and stable bioorthogonal reactants in the Carboni-Lindsey reaction." Angewandte Chemie 128.40 (2016): 12431-12435.
Huang et al. "Repurposing psychiatric drugs as anti-cancer agents." Cancer Letters 419 (2018): 257-265.
International Search Report and Written Opinion in corresponding International Patent Application No. PCT/EP2020/074529 mailed Nov. 13, 2020. 13 pages.
Manara et al. "MLL-AF6 fusion oncogene sequesters AF6 into the nucleus to trigger RAS activation in myeloid leukemia." Blood, The Journal of the American Society of Hematology 124.2 (2014): 263-272.
Masetti et al. "CBFA2T3-GLIS2 fusion transcript is a novel common feature in pediatric, cytogenetically normal AML, not restricted to FAB M7 subtype." Blood, The Journal of the American Society of Hematology 121.17 (2013): 3469-3472.
Nagel et al. "Pharmacologic inhibition of MALT1 protease by phenothiazines as a therapeutic approach for the treatment of aggressive ABC-DLBCL." Cancer cell 22.6 (2012): 825-837.
Pession et al. "Results of the AIEOP AML Jan. 2002 multicenter prospective trial for the treatment of children with acute myeloid leukemia." Blood, The Journal of the American Society of Hematology 122.2 (2013): 170-178.
Pigazzi et al. "MLL partner genes drive distinct gene expression profiles and genomic alterations in pediatric acute myeloid leukemia: an AIEOP study." Leukemia 25.3 (2011): 560-563.
Pigazzi et al. "Screening of novel genetic aberrations in pediatric acute myeloid leukemia: a report from the AIEOP AML-2002 study group." Blood, The Journal of the American Society of Hematology 120.18 (2012): 3860-3862.

(Continued)

*Primary Examiner* — Shobha Kantamneni
(74) *Attorney, Agent, or Firm* — Leason Ellis LLP

(57) ABSTRACT

The present invention relates to novel thioridazine analogue compounds of formula (I): wherein $R_1$ is $OCH_3$ or $NH_2$, particularly suitable to be used in the treatment of pediatric acute myeloid leukemia harboring the t(6;11)(q27;q23) KMT2A/AFDN rearrangement.

(I)

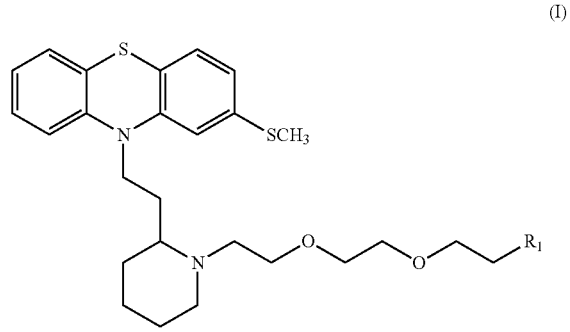

5 Claims, 4 Drawing Sheets

(56) References Cited

OTHER PUBLICATIONS

Pritchard-Jones et al. "Sustaining innovation and improvement in the treatment of childhood cancer: lessons from high-income countries." The lancet oncology 14.3 (2013): e95-e103.

Pui et al. "Biology, risk stratification, and therapy of pediatric acute leukemias: an update." Journal of clinical oncology 29.5 (2011): 551.

Schlauderer et al. "Structural analysis of phenothiazine derivatives as allosteric inhibitors of the MALT1 paracaspase." Angewandte Chemie International Edition 52.39 (2013): 10384-10387.

Tefferi. "Somatic JAK2 mutations and their tumor phenotypes." Blood, The Journal of the American Society of Hematology 128.6 (2016): 748-749.

Vallée et al. "Staudinger-phosphonite reactions for the chemoselective transformation of azido-containing peptides and proteins." Organic Letters 13.20 (2011): 5440-5443.

Zampini et al. "A three-miRNA-based expression signature at diagnosis can predict occurrence of relapse in children with t (8; 21) RUNX1-RUNX1T1 acute myeloid leukaemia." British journal of haematology 183.2 (2017): 298-301.

Zhelev et al. "Phenothiazines suppress proliferation and induce apoptosis in cultured leukemic cells without any influence on the viability of normal lymphocytes." Cancer Chemotherapy and Pharmacology 53.3 (2004): 267-275.

Zwaan et al. "Collaborative efforts driving progress in pediatric acute myeloid leukemia." Journal of clinical oncology 33.27 (2015): 2949.

A

B

C

THIORIDAZINE DERIVATIVES AND THEIR USE FOR THE TREATMENT OF CANCER

CROSS-REFERENCE TO RELATED PATENT APPLICATIONS

This application is a U.S. National Stage Application under 35 U.S.C. § 371 of International Patent Application No. PCT/EP2020/074529 filed Sep. 3, 2020, which claims the benefit of priority of Italian Patent Application No. 102019000015809 filed Sep. 6, 2019, both of which are incorporated by reference in their entireties. The International Application was published on Mar. 11, 2021, as International Publication No. WO 2021/043862 A1.

FIELD OF THE INVENTION

The present invention relates to novel thioridazine analogue compounds, particularly suitable to be used in the treatment of pediatric acute myeloid leukemia harboring the t(6;11)(q27;q23) KMT2A/AFDN rearrangement.

BACKGROUND

Acute leukemias account for approximately one third of all pediatric malignancies and cause a great number of the cancer-related deaths in children. Acute myeloid leukemia (AML) accounts for approximately the 15-20% of childhood leukemia at diagnosis with a survival rate of 67% in the last concluded Italian trial (Pession A, Masetti R, Rizzari C, Putti M C, Casale F, Fagioli F, et al. Results of the AIEOP AML 2002/01 multicenter prospective trial for the treatment of children with acute myeloid leukemia. Blood. 2013; 122: 170-8). Importantly, 30% of patients experience disease recurrence, which is still the major cause of treatment failure and death in these patients (Pession A. et al, op. cit.). Although recurrent chromosomal rearrangements and mutations are established prognostic markers able to tailor a risk-adapted therapy (Zampini M, Bisio V, Leszl A, Putti M C, Menna G, Rizzari C, et al. A three-miRNA-based expression signature at diagnosis can predict occurrence of relapse in children with t(8;21) RUNX1-RUNX1T1 acute myeloid leukaemia. Br J Haematol [Internet]. 2017;1-4. Available from: http://doi.wiley.com/10.1111/bjh.14950; Bisio V, Zampini M, Tregnago C, Manara E, Salsi V, Di Meglio a, et al. NUP98-fusion transcripts characterize different biological entities within acute myeloid leukemia: a report from the AIEOP-AML group. Leukemia [Internet]. 2017; 31:974-7. Available from: http://www.nature.com/doifinder/10.1038/leu.2016.361; Masetti R, Pigazzi M, Togni M, Astolfi A, Indio V, Manara E, et al. CBFA2T3-GLIS2 fusion transcript is a novel common feature in pediatric, cytogenetically normal AML, not restricted to FAB M7 subtype. Blood [Internet]. 2013 [cited 2014 May 26];121:3469-72. Available from: http://www.ncbi.nlm.nih.qov/pubmed/23407549; Pigazzi M, Manara E, Bisio V, Aveic S, Masetti R, Menna G, et al. Screening of novel genetic aberrations in pediatric acute myeloid leukemia: a report from the AIEOP AML-2002 study group. Blood [Internet]. 2012 [cited 2014 May 26];120:3860-2. Available from: http://www.ncbi.nlm-.nih.qov/pubmed/23118215), the ongoing prospective clinical trials run by pediatric leukemia international cooperative groups still employ four to five courses of intensive myelosuppressive chemotherapy in standard risk AML patients, reserving the use of allogeneic hematopoietic stem cell transplantation (HSCT) to either relapsed children or patients in first complete remission but with a high-risk of disease recurrence (Pession A. et al, op. cit.; Zwaan C M, Kolb E a., Reinhardt D, Abrahamsson J, Adachi S, Aplenc R, et al. Collaborative Efforts Driving Progress in Pediatric Acute Myeloid Leukemia. J Clin Oncol. 2015; 33:2949-62; Pui C-H, Carroll W L, Meshinchi S, Arceci R J. Biology, risk stratification, and therapy of pediatric acute leukemias: an update. J Clin Oncol. 2011; 29:551-65). However, this therapeutic approach is unsatisfactory in terms of toxicity, with a persistent risk of relapse due to the escape of quiescent leukemic cells to chemotherapy. To date the development of new drugs for pediatric cancer is hampered by peculiar obstacles, including the small number of patients available for clinical trials, the heterogeneity of leukemia subclones (Duque-Afonso J, Cleary M L. The AML salad bowl. Cancer Cell. 2014. page 265-7), as well as the strict safety limitations for pediatric drugs, all together seriously limiting drug discovery (Vassal G, Zwaan C M, Ashley D, Le Deley M C, Hargrave D, Blanc P, et al. New drugs for children and adolescents with cancer: the need for novel development pathways. Lancet Oncol [Internet]. 2013 [cited 2015 Jul. 17];14:e117-24. Available from: http://www.ncbi.nlm.nih.gov/pubmed/23434337).

Among the pediatric AML, those harboring t(6;11)(q27;q23) chromosomal rearrangement are the most aggressive leukemia, with a intolerably low rate of event-free survival (11-23% at 5 years) (Balgobind B V, Raimondi S C, Harbott J, Zimmermann M, Alonzo T A, Auvrignon A, et al. Novel prognostic subgroups in childhood 11q23/MLL-rearranged acute myeloid leukemia: results of an international retrospective study. Blood [Internet]. 2009 [cited 2015 Jul. 7];114:2489-96. Available from:
http://www.pubmedcentral.nih.gov/articlerender.fcqi?artid=2927031&tool=pmcentrez&rendertype=abstract; Pigazzi M, Masetti R, Bresolin S, Beghin A, Di Meglio A, Gelain S, et al. MLL partner genes drive distinct gene expression profiles and genomic alterations in pediatric acute myeloid leukemia: an AIEOP study. Leukemia. 2011; 25:560-3). Biologically, in this subset of pediatric AML the genes Lysine Methyltransferase 2A (KMT2A, MLL) and Afadin (AFDN, AF6) are fused together generating the chimeric protein MLL-AF6 (Pigazzi M, Masetti R et al. op. cit.; Manara E, Baron E, Tregnago C, Aveic S, Bisio V, Bresolin S, et al. MLL-AF6 fusion oncogene sequesters AF6 into the nucleus to trigger RAS activation in myeloid leukemia. Blood. 2014; 124:263-72), which drives peculiar gene expression and biological features supporting their aggressiveness.

Tregnago C. presented at ASH congress (Blood 2016, 128:749) preliminary data on thioridazine (TDZ) as a novel therapeutic opportunity for pediatric patients with AML harboring t(6;11)(q27;q23) chromosomal rearrangement.

The Applicant noted that TDZ is a neuroleptic drug, which present limitations to be overcome for its use, since it may generate side effects on central nervous system (CNS), especially when administered on pediatric patients.

SUMMARY OF INVENTION

An object of the present invention is therefore the provision of new compounds specifically targeting AML harboring t(6;11)(q27;q23) chromosomal rearrangement, not generating side effects on CNS and thus especially safe for pediatric application.

Therefore, the present invention relates, in a first aspect, to a thioridazine analogue compound of formula (I):

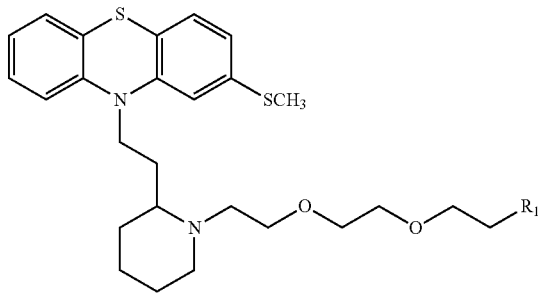

(I)

wherein $R_1$ is $OCH_3$ or $NH_2$.

The Applicant has indeed unexpectedly found out that the compound of formula (I) according to the present invention, shows high cytotoxic activity on pediatric acute myeloid leukemia harboring the t(6;11)(q27;q23) KMT2A/AFDN rearrangement, without generating side effects on CNS and is thus especially safe for pediatric applications.

Without being bound to any theory, the inventors deem that the compound of formula (I) triggers a rise in intracellular $Ca^{2+}$ concentration in the presence, but not in the absence, of external $Ca^{2+}$, suggesting a selective increase of $Ca^{2+}$ entry over internal release. This latter constitutes a novel cell death mechanism never exploited in pediatric AML, to knowledge of the Applicant.

In a further aspect, therefore, the present invention also relates to the compound of formula (I) according to the present invention, for use as a medicament.

The Applicant has indeed unexpectedly found out that the compound of formula (I) is suitable for use as a medicament, and particularly for specifically targeting AML cells harboring t(6;11)(q27;q23) chromosomal rearrangement, without generating side effects on CNS and thus especially safe for pediatric application.

In a still further aspect, the present invention also relates to the compound of formula (I) according to the present invention for use in the treatment of a tumor, particularly an acute myeloid leukemia and especially a pediatric acute myeloid leukemia harboring the t(6;11)(q27;q23) KMT2A/AFDN rearrangement.

DETAILED DESCRIPTION OF THE INVENTION

Figure 1:
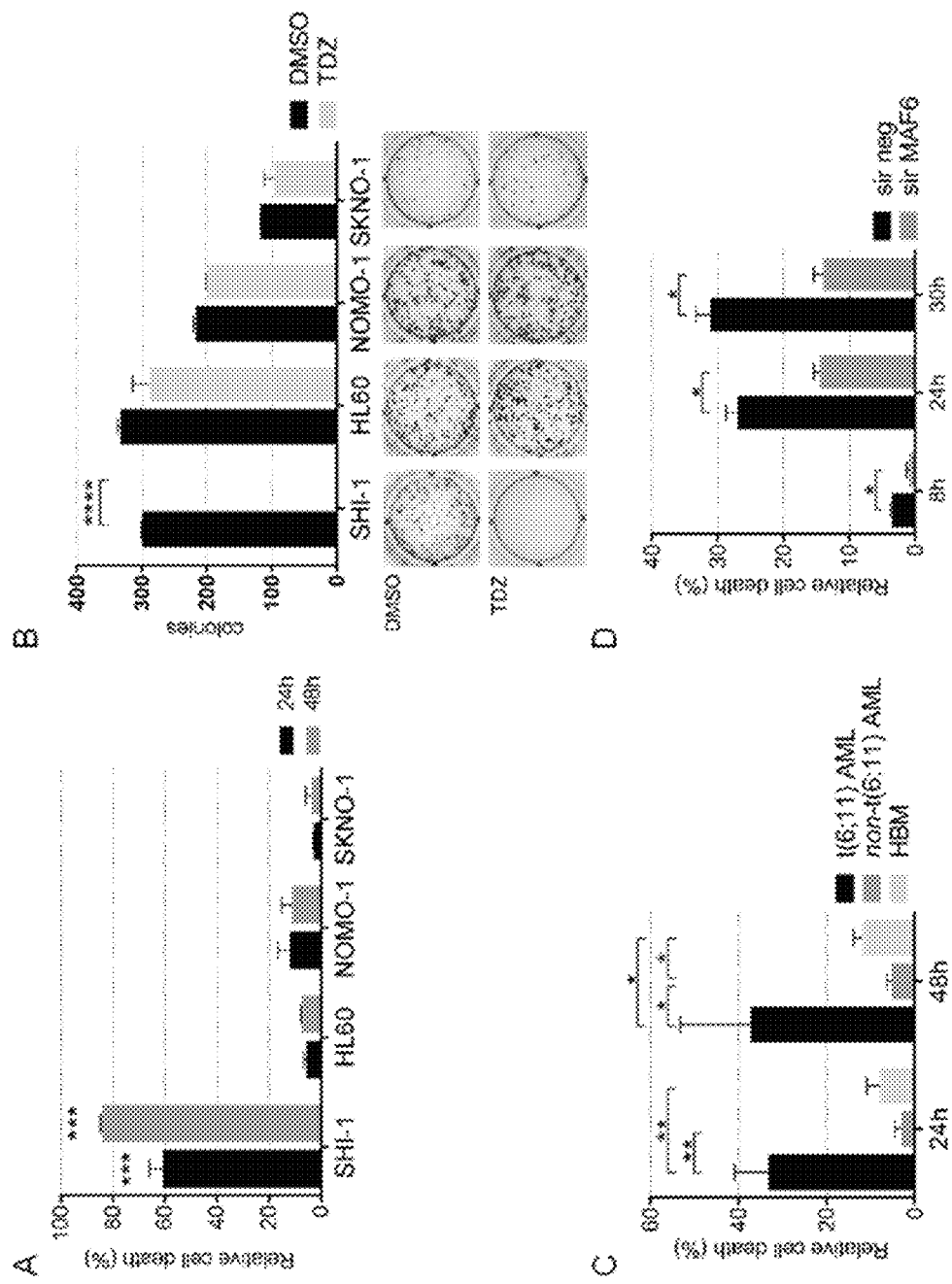
FIG. 1 shows the apoptosis assay carried out with tioridazine (TDZ), and its colony-forming ability on viable t(6;11) SHI-1 and non-t(6;11) HL60, NOMO-1, SKNO-1 cells. Data are presented as mean±SEM. *P<0.05; P<0.01; *P<0.001.

The present invention relates, in a first aspect, to a thioridazine analogue compound of formula (I):

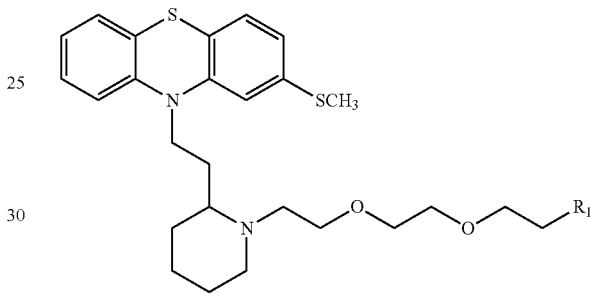

(I)

wherein $R_1$ is $OCH_3$ or $NH_2$.

The Applicant has indeed unexpectedly found out that the compound of formula (I) according to the present invention, shows high cytotoxic activity on pediatric acute myeloid leukemia harboring the t(6;11)(q27;q23) KMT2A/AFDN rearrangement, without generating side effects on CNS and is thus especially safe for pediatric applications.

The present invention may present in one or more of the above aspects one or more of the characteristics disclosed hereinafter.

In a preferred embodiment, in the compound of formula (I) $R_1$ is $OCH_3$.

In a further preferred embodiment, in the compound of formula (I) $R_1$ is $NH_2$.

In a further aspect, the present invention also relates to the compound of formula (I) according to the present invention, for use as a medicament.

The compounds of the invention may be administered by systemic administration including oral administration and parenteral administration.

The compounds of the invention may be administered once or according to a dosing regimen wherein a number of doses are administered at varying intervals of time for a given period of time. Doses may be combined to front line chemotherapy according to the TRIAL when included. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan.

The compounds of the invention will be normally, but not necessarily, formulated into a pharmaceutical composition prior to administration to a patient. The pharmaceutical compositions of the invention are prepared using techniques and methods known to those skilled in the art.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. A dose of the pharmaceutical composition contains at least a therapeutically effective amount of a compound of this invention as indicated by phase-I and II trials.

The compounds of the invention and the pharmaceutically acceptable excipient or excipients will typically be formulated into a dosage form adapted for administration to the patient by the desired route of administration.

Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution.

Suitable pharmaceutically acceptable excipients include the following types of excipients: diluents, fillers, binders, disintegrants, lubricants, granulating agents, coating agents, wetting agents, suspending agents, emulsifiers, sweeteners, flavour masking agents, colouring agents, anti-caking agents, humectants, plasticizers, viscosity increasing agents, antioxidants, preservatives, stabilizers, surfactants, and buffering agents. Suitable diluents and fillers include lactose, sucrose, dextrose, mannitol, sorbitol, starch, cellulose, calcium sulphate, and dibasic calcium phosphate. The oral solid dosage form may further comprise a binder. Suitable binders include starch, gelatin, sodium alginate, alginic acid, guar gum, povidone, and cellulose and its derivatives (e.g. microcrystalline cellulose). The oral solid dosage form may further comprise a disintegrant. Suitable disintegrants include crospovidone, sodium starch glycolate, alginic acid, and sodium carboxymethyl cellulose. The oral solid dosage form may further comprise a lubricant. Suitable lubricants include stearic acid, magnesium stearate, calcium stearate, and talc. Suitable carriers for oral dosage forms include but are not limited to magnesium carbonate, magnesium stearate, talc, lactose, pectin, dextrin, starch, methylcellulose, sodium carboxymethyl cellulose, and the like. Techniques used to prepare oral formulations are the conventional mixing, granulation and compression or capsules filling.

The compounds of the present invention may be also formulated for parenteral administration with suitable carriers including aqueous vehicles solutions (i.e.: saline, dextrose) or and/or oily emulsions.

The Applicant has indeed unexpectedly found out that the compound of formula (I) is suitable for use as a medicament, and particularly for specifically targeting AML cells harboring t(6;11)(q27;q23) chromosomal rearrangement, without generating side effects on CNS and thus especially safe for pediatric application.

In a still further aspect, the present invention also relates to the compound of formula (I) according to the present invention for use in the treatment of a tumor.

Preferably, said tumor is an acute myeloid leukemia and more preferably a pediatric acute myeloid leukemia harboring the t(6;11)(q27;q23) KMT2A/AFDN rearrangement.

Further features and advantages of the invention will appear more clearly from the following description of some preferred embodiments thereof, made hereinafter by way of a non-limiting example with reference to the following exemplary examples.

Experimental Part

Methods

Apoptosis Assay

Apoptosis was evaluated by double staining with Annexin-V/propidium iodide (Roche Biochemicals, Indianapolis, IN) and analyzed using Cytometer F C500 (Beckman Coulter, Brea, CA). Increased apoptosis was calculated and expressed as the percentage of Annexin-V-positive and propidium iodide-positive cells compared to those exposed to DMSO.

Colonies Forming Assay

After 24 h of treatment, a total of $5\times10^2$ ML2, SHI-1, HL60, SKNO-1 or NOMO-1 cells and $3\times10^3$ primary blasts from patients with t(6;11)—rearranged AML were seeded into 500 μl of MethoCult™ (H4230 and H4534 respectively, Stemcell Technologies, Meda M B, Italy), in 24-well plates and incubated at 37° C. Fourteen days after seeding, an adequate volume of a 1:6 solution of 3-[4,5-dimethylthiazol-2-yl]-2,5-diphenyltetrazolium bromide (MTT, Sigma-Aldrich-Merck) in Hanks' was added to semisolid medium. Images were acquired by optical microscope with camera, and colonies were counted using ImageJ software.

Measurements of Intracellular $Ca^{2+}$

Intracellular $Ca^{2+}$ levels were monitored by Fluo-4 AM fluorescence according to the manufacturer's instructions. Briefly, cells were washed in Hanks Balanced Salt Solutions, incubated with Fluo-4 AM 3 μM diluted in the working buffer (0.02% w/v Pluronic and 0.2 mM sulfinpyrazone, both sourced from Sigma-Aldrich-Merck, in 10 mM HEPES-buffered Hanks) for 30' at RT. After incubation, cells were washed and resuspended in working buffer with $CaCl_2$) 0.2 mg/l for 30', to allow the de-esterification of Fluo-4 AM. Results were evaluated using the FC500 cytometer, and 2-photon microscope Thorlabs. In both experiments, the mean fluorescence intensity (MFI) was detected at basal condition, and up to 5 minutes after treatment.

Reactive Oxygen Species (ROS)

ROS production was monitored by flow cytometry using CellROX Deep Red Reagent (C10422, Invitrogen) following manufacturer's instructions. Briefly, CellROX Deep Red Reagent was added at a final concentration of 5 μM to the cells and incubated for 30 minutes at 37° C. Cells were washed three times with PBS, and analyzed by flow cytometry using Cytoflex (Beckman Coulter).

Mitochondrial Membrane Potential

Mitochondrial membrane potential was measured by using TMRE Assay Kit (ab113852, Abcam), following manufacturer's instructions Briefly, TMRE 200 nM diluted in BSA 0.2%-PBS1× was added for 20' at 37° C. Cells were analyzed by flow cytometry using FC500.

Flank Injection Xenograft Experiments

Animal experiments were approved by the animal ethics committee of University of Padova and by Italian Minister of Health n° 512/2019-PR, and were executed in accordance with national guidelines and regulations. For flank injection experiments, six NOD-SCID interleukin-2 receptor gamma null (NSG) mice between 6 and 8 weeks of age were injected subcutaneously with $2\times10^6$ SHI-1, HL60 or THP-1 cells per flank-injection. Each mouse received two flank-injections. When tumors reached an area of 25 mm$^2$, mice were randomized in 2 groups (control and TDZ-treated), and daily treated with intraperitoneally (ip) administered TDZ 8 mg/kg. Experimental endpoint is reached when tumors reached an area of 250 mm$^2$.

Stepping Test

Twelve NSG mice between 6 and 8 weeks of age were randomized in 4 groups (DMSO, thioridazine (TDZ), compound according to Example 1 (TDZ2) and compound according to Example 2 (TDZ6)), and treated every 2 days with growing doses of drugs, administered ip. The starting dose was 8 mg/kg of TDZ, previously tested to be free of side effects, and the corresponding molar dose of the analogues TDZ2 and TDZ6. The successive growing doses were 10 mg/kg, 12 mg/kg and finally 15 mg/kg, and the corresponding molar dose of the analogues. The stepping test was performed as previously described (Blume S R, Cass D K, Tseng K Y. Stepping test in mice: A reliable approach in determining forelimb akinesia in MPTP-induced Parkinsonism. Exp Neurol. 2009; 219:208-11) 1 h after drug injection, documented to be the time with the maximum TDZ serum concentration (Nagel D, Spranger S, Vincendeau M, Grau M, Raffegerst S, Kloo B, et al. Pharmacologic Inhibition of MALT1 Protease by Phenothiazines as a Therapeutic Approach for the Treatment of Aggressive ABC-DLBCL. Cancer Cell. 2012; 22:825-37). Briefly, the stepping test was performed on an open table and each trial was recorded using a digital video camera. The animal was allowed to settle at one edge of the table, then the experimenter would lift up the hind legs by pulling up on the tail, leaving only the forepaws touching the table, for a total distance of 1 m. The number of steps from both forepaws and the time used were computed.

Example 1—Synthesis of a Compound of Formula (I) Wherein $R_1$ is $OCH_3$ (TDZ2)

TDZ2 was prepared following a concise three-step synthetic procedure reported in the Scheme 1. Following a previously reported synthesis (Schlauderer F, Lammens K, Nagel D, Vincendeau M, Eitelhuber A C, Verhelst SHL, et al. Structural analysis of phenothiazine derivatives as allosteric inhibitors of the MALT1 paracaspase. Angew Chemie—Int Ed. 2013; 52:10384-7), commercially available racemic TDZ was N-demethylated by treatment with 1-chloroethyl-chloroformate in refluxing DCE followed by hydrolysis with MeOH under reflux, leading to derivative 2. The subsequent $S_N2$ nucleophilic substitution reaction with tosyl triethylene glycol methyl ether derivative 3 in refluxing acetonitrile, in presence of $K_2CO_3$ as base, to yield the N-alkylated product TDZ2. The bifunctional polyethylene glycol (PEG) linker 3 was prepared as described earlier (Vallée MRJ, Majkut P, Wilkening I, Weise C, Müller G, Hackenberger CPR. Staudinger-phosphonite reactions for the chemoselective transformation of azido-containing peptides and proteins. Org Lett. 2011; 13:5440-3).

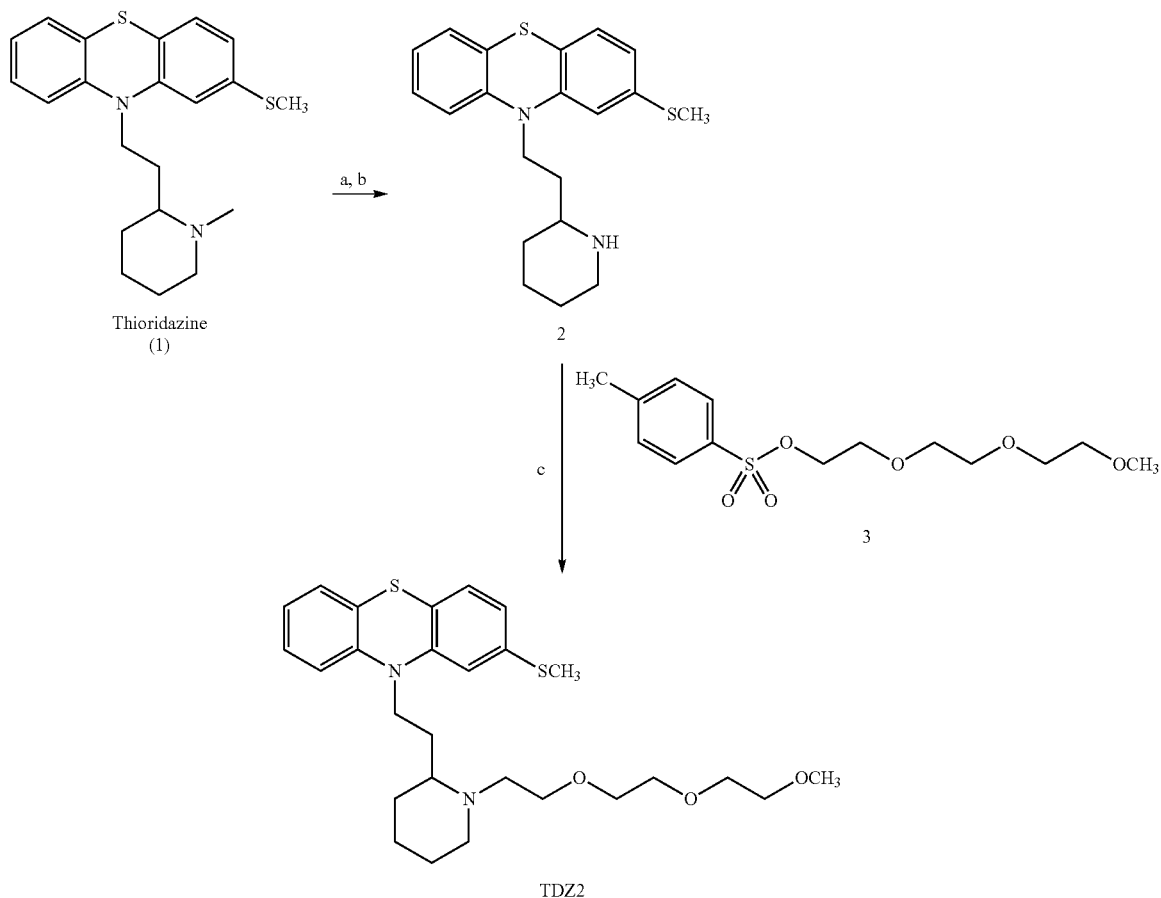

Scheme 1

Reagents. a) 1-chloro-ethylchloroformate, 1,2-dichloroethane, reflux, 12 h; b). MeOH, reflux, 12 h; c) tosyl triethylene glycol methyl ether (3), K₂CO₃, CH₃CN, reflux, 48 h.

Example 2—Synthesis of a Compound of Formula (I) Wherein R₁ is NH₂ (TDZ6)

TDZ6 was prepared following a concise three-step synthetic procedure reported in the Scheme 2. Following a previously reported synthesis (Schlauderer F, Lammens K, Nagel D, Vincendeau M, Eitelhuber A C, Verhelst SHL, et al. Structural analysis of phenothiazine derivatives as allosteric inhibitors of the MALT1 paracaspase. Angew Chemie—Int Ed. 2013; 52:10384-7), commercially available racemic TDZ was N-demethylated by treatment with 1-chloroethyl-chloroformate in refluxing DCE followed by hydrolysis with MeOH under reflux, leading to derivative 2. The subsequent S$_N$2 nucleophilic substitution reaction with azido tosylate derivative 3 in refluxing acetonitrile, in presence of K₂CO₃ as base, to yield the N-alkylated product. The efficient Staudinger reduction at room temperature enables the preparation of amine TDZ6 in excellent yield. The bifunctional polyethylene glycol (PEG) linker 3 was prepared as described earlier (Eising S, Lelivelt F, Bonger K M. Vinylboronic Acids as Fast Reacting, Synthetically Accessible, and Stable Bioorthogonal Reactants in the Carboni-Lindsey Reaction. Angew Chemie—Int Ed. 2016; 55:12243-7).

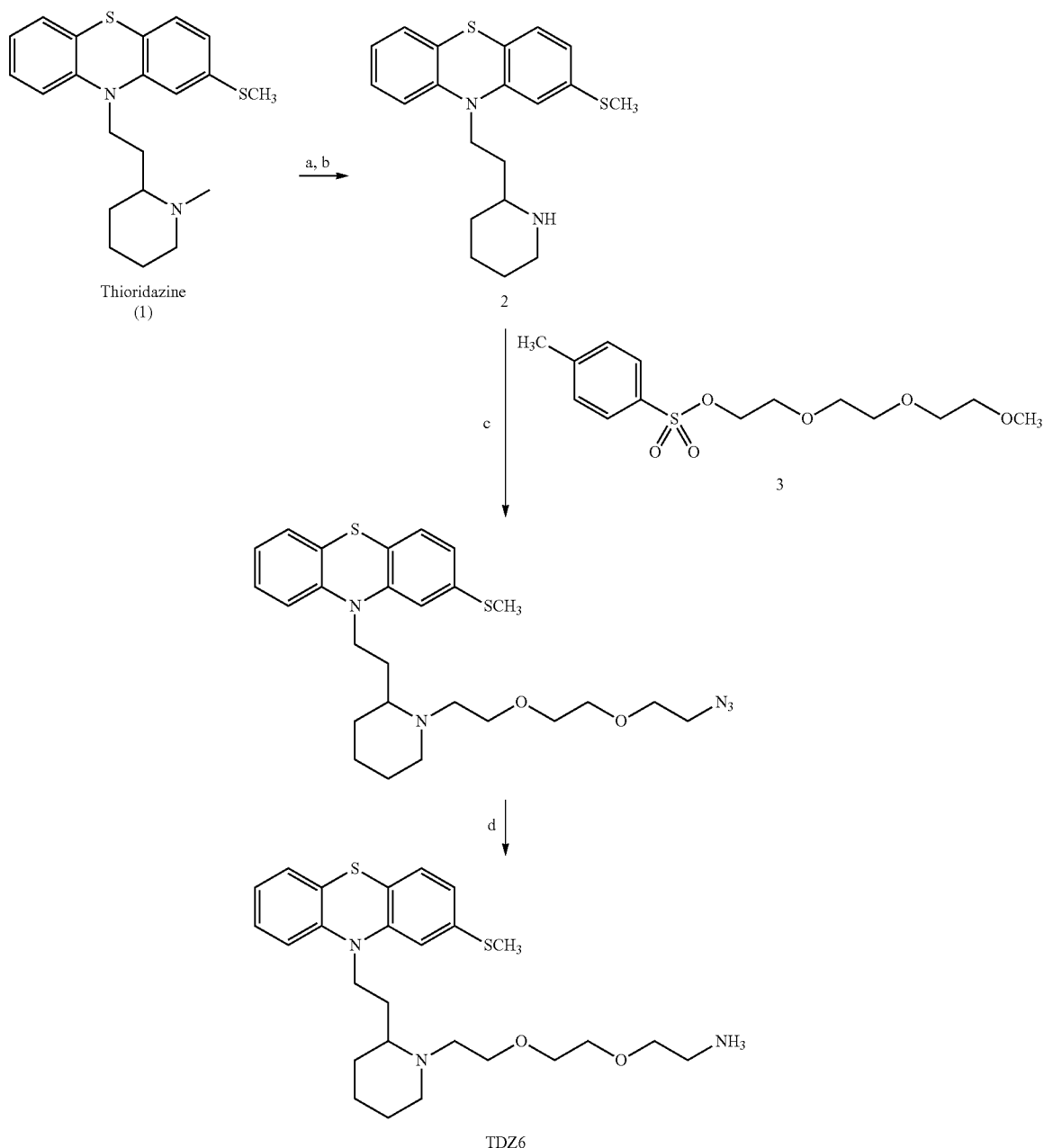

Scheme 2

Reagents. a) 1-chloro-ethylchloroformate, 1,2-dichloroethane, reflux, 12 h; b). MeOH, reflux, 12 h; c) 2-(2-(2-azidoethoxy)ethoxy)ethyl 4-m ethylbenzenesulfonate (3), $K_2CO_3$, $CH_3CN$, reflux, 48 h; d) $Ph_3P$, water, room temperature, 24 h Reference Example 1-Tests on TDZ Tests carried out with tioridazine (TDZ), showed the results reported in FIGS. 1, 2 and 3.

Notably, in an in vitro experiment by means of the apoptosis assay, by using the SHI-1, an AML cell line with the genetic aberrancy t(6;11), TDZ showed strongly increased apoptosis and cell death in since 24 hours (h) of treatment (apoptotic and dead cells: 60.8% and 84.3% at 24 and 48 h, respectively), with almost no effects in other AML cell lines harboring other genetic mutations (HL60, NOMO1, SKNO-1). In this regard, FIG. 1 (A) shows the cell death (Annexin V+, PI+ and Annexin V+/PI+) induced by TDZ in t(6;11) SHI-1 and non-t(6;11) HL60, NOMO-1, SKNO-1 cell lines 24 and 48 h after treatment, relative to DMSO value.

Furthermore, investigating self-renewal ability, it was found that after 24 h of pre-treatment with TDZ, $5\times10^2$ viable cells (defined by trypan blue exclusion) seeded in drug-free condition abrogated colony-forming ability. In addition, 24 h of TDZ treatment did not decrease the clonogenic potential of other AML cell lines.

In this regard, FIG. 1 (B) shows the colony-forming assay performed on viable t(6;11) SHI-1 and non-t(6;11) HL60, NOMO-1, SKNO-1 cells, seeded 24 h after TDZ treatment (n=3). Representative images of colonies are shown in the lower panel.

The TDZ efficacy was also validated on primary cells derived from patients with AML: TDZ induced apoptosis selectively in primary cultures from patients with t(6;11) AML, compared with non-t(6;11)—AML, whereas no toxic effects were shown on healthy bone marrow (HBM) cells; moreover, TDZ abrogated colony-forming ability of t(6;11)—AML primary cells, but not on HBM.

In this regard, FIG. 1 (C) shows the cell death (Annexin V+, PI+ and Annexin V+/PI+) of t(6;11), non-t(6;11) primary AML samples (n=3 and 6, respectively), and HBM (n=4), 24 and 48 h after TDZ treatment, compared with DMSO value.

To confirm these findings, genetic engineering was used to silence the gene producing the MLL-AF6 chimera in SHI-1 and to test if the sensitivity to TDZ was still present in the absence of MLL-AF6. The results documented that TDZ treatment performed 16 h after MLL-AF6 silencing resulted in a significant rescue of apoptosis level at 8, 24 and 30 h after treatment.

In this regard, FIG. 1(D) shows the cell death (Annexin V+, PI+ and Annexin V+/PI+) of SHI-1 cells treated with TDZ 16 h after MLL-AF6 chimera silencing, evaluated 8, 24 and 30 h after treatment (n=2), compared with DMSO value.

Thus, TDZ showed death effects when AML cells specifically produced the MLL-AF6 protein, being highly selective for this AML subgroup.

TDZ was also used for further tests and particularly to test if it had same effects on leukemia growth in vivo in NOD/scid IL-2Rgnull (NSG) mice flank-injected with the SHI-1-t(6;11) or non-t(6;11) AML cell lines HL60 and THP-1. Xenografted tumor was allowed to grow up to ~75 $mm^2$ before starting daily intraperitoneal (i.p.) TDZ administration (at 8 mg/kg concentration, below the previously described tolerated dose (Nagel D, Spranger S, Vincendeau M, Grau M, Raffegerst S, Kloo B, et al. Pharmacologic Inhibition of MALT1 Protease by Phenothiazines as a Therapeutic Approach for the Treatment of Aggressive ABC-DLBCL. Cancer Cell. 2012; 22:825-37)).

Figure 2:
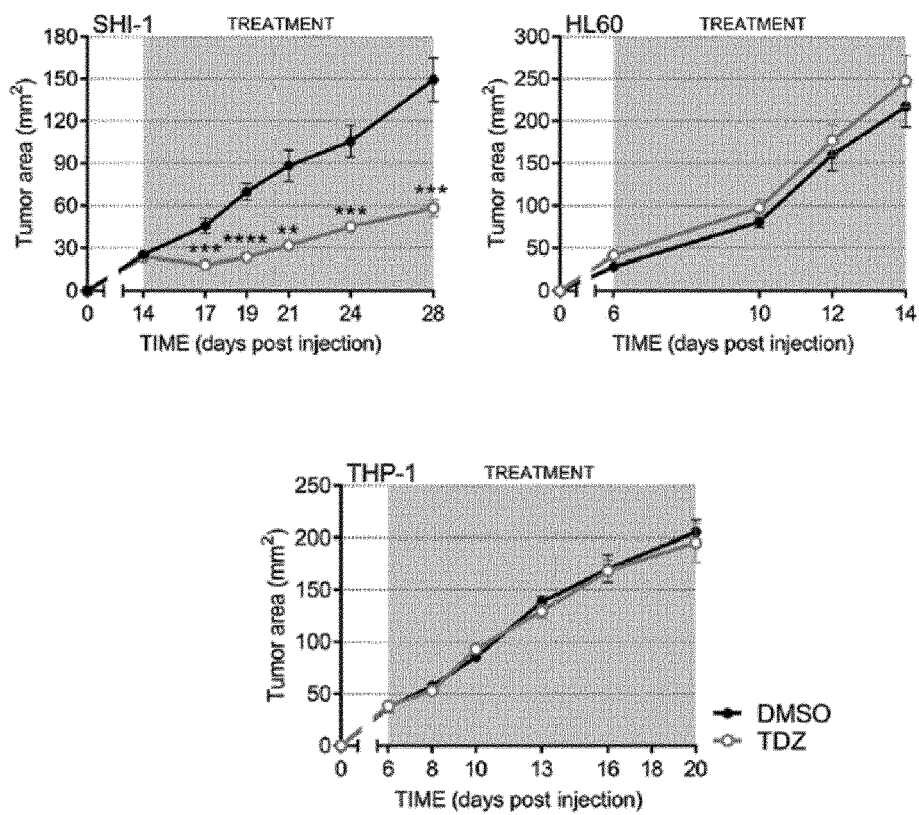
FIG. 2 shows the tumor growth in mice flank-injected with t(6;11) SHI-1 and non-t(6;11) HL60 or THP1 cells treated with TDZ, the ROS levels detected after TDZ treatment in t(6;11) SHI-1 cells, and Mitochondrial depolarization evaluated through TMRE measurement after TDZ treatment in t(6;11) SHI-1 cells. Data are presented as mean±SEM. *P<0.05; P<0.01; *P<0.001.
Figure 2:
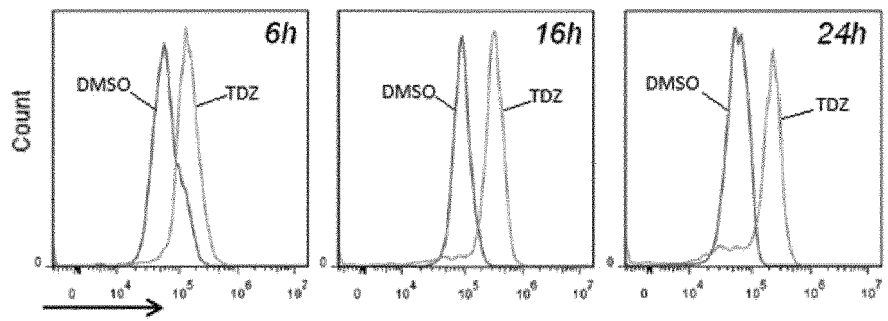
Figure 2:
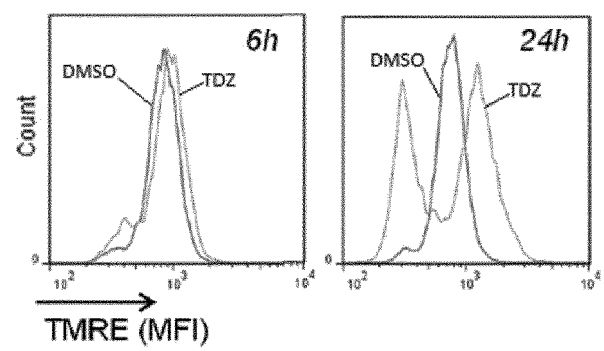

In this regard, FIG. 2 (A) shows the tumor growth in mice flank-injected with t(6;11) SHI-1 and non-t(6;11) HL60 or THP1 cells and daily treated with TDZ 8 mg/kg (grey area), compared with the control group treated with DMSO (n=6).

As it is clear from FIG. 2 (A), only in SHI-1 xenografted mice the treatment significantly reduced the progression of tumor growth compared with control (treated with vehicle, $p<0.01$ and $p<0.001$). Oppositely, tumor growth in mice xenografted with HL60 or THP1 was not affected by TDZ treatment.

In order to unveil the mechanism underlying cell death, highly increased reactive oxygen species (ROS) after TDZ treatment in SHI-1 was also measured, resulting in a mitochondrial depolarization that supported the apoptosis induction.

In this regard, FIG. 2 (B) shows the ROS levels detected 6, 16 and 24 h after TDZ treatment compared with DMSO, in t(6;11) SHI-1 cells and FIG. 2 (C) shows the mitochondrial depolarization evaluated through TMRE measurement, 6 and 24 h after TDZ treatment compared with DMSO, in t(6;11) SHI-1 cells.

Calcium ($Ca^{2+}$) influx upon TDZ treatment was also measured.

Figure 3:
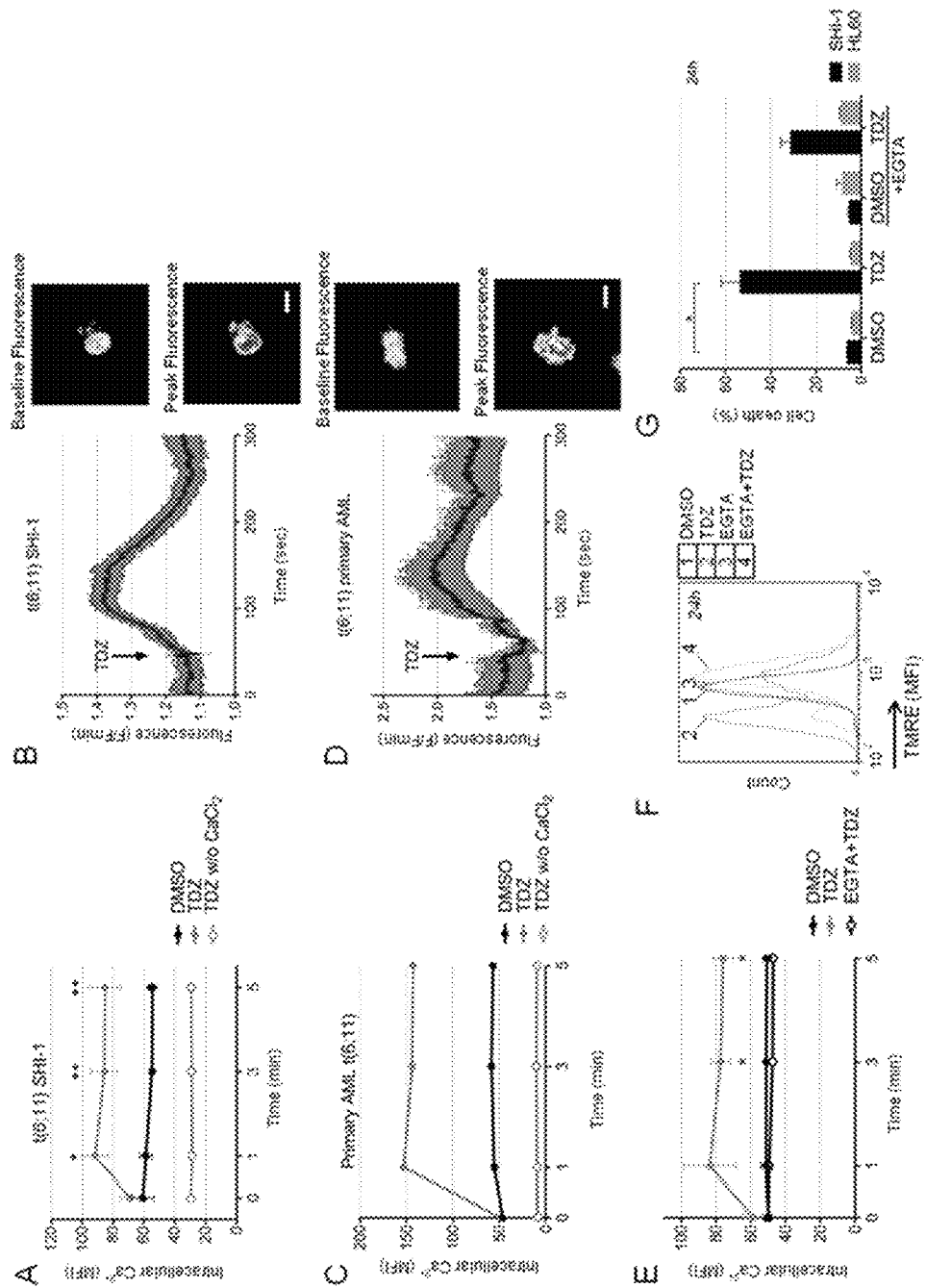
FIG. 3 shows the live intracellular $Ca^{2+}$ measurement in SHI-1 cells loaded with Fluo-4 AM $Ca^{2+}$ indicator in presence of a TDZ treatment, the histograms overlay showing mitochondrial depolarization evaluated through TMRE measurement after TDZ, ethylene glycol-bis(β-aminoethyl ether)-N,N,N',N'-tetraacetic acid (EGTA) or EGTA+ TDZ treatment, and the apoptosis assay carried out with TDZ, EGTA or EGTA+ TDZ treatment in t(6;11) SHI-1 and non-t(6;11) HL60. Data are presented as mean±SEM. *P<0.05; **P<0.01.

FIG. 3 (A-B) shows the live intracellular $Ca^{2+}$ measurement in SHI-1 cells loaded with Fluo-4 AM $Ca^{2+}$ indicator. Intracellular $Ca^{2+}$ measurement by flow cytometry is shown in FIG. 3 (A) (DMSO MFI results: 60.6, 58.6, 54.7, 54.6 and TDZ MFI: 68.9, 91.8, 85.8, 85.4) at 0, 1, 3 and 5 minutes post treatment, respectively. Of note, TDZ triggers a rise in intracellular $Ca^{2+}$ concentration in the presence, but not in the absence, of external $Ca^{2+}$, suggesting a selective increase of $Ca^{2+}$ entry over internal release (in $Ca^{2+}$-containing or in $Ca^{2+}$-free buffer, as indicated in the legend). FIG. 3 (B) shows the intracellular $Ca^{2+}$ measurement by 2-photon microscope: arrow indicates TDZ treatment; cell images show baseline vs peak fluorescence. This latter constituted a novel TDZ-induced cell death mechanism never exploited in pediatric AML, to knowledge of the Applicant.

To support this finding of $Ca^{2+}$ homeostasis as a new feature to target t(6;11) AML cells, the same pathway on AML cells collected from patients was also investigated, confirming also in primary cultures that TDZ treatment increased cytosolic $Ca^{2+}$ influx in t(6;11) AML.

In this regard, FIG. 3 (C-D) shows the live intracellular $Ca^{2+}$ in t(6;11) primary cells loaded with Fluo-4 AM $Ca^{2+}$ indicator, measured by flow cytometry in FIG. 3 (C) in $Ca^{2+}$-containing, or in $Ca^{2+}$+-free buffer, or by 2-photon microscope in FIG. 3 (D) (arrow indicate TDZ treatment and images show baseline vs peak fluorescence).

To validate this phenomenon, SHI-1 cells were pre-treated with the extracellular $Ca^{2+}$ chelator ethylene glycol-bis(β-aminoethyl ether)-N, N, N',N'-tetraacetic acid (EGTA).

FIG. 3 (E) shows the live intracellular $Ca^{2+}$ measurement in SHI-1 cells loaded with Fluo-4 AM $Ca^{2+}$ indicator, measured by flow cytometry: EGTA pre-treatment was performed 30' before TDZ.

As it is clear from FIG. 3 (E), $Ca^{2+}$ intake was prevented, confirming that TDZ treatment led to external $Ca^{2+}$ influx. Furthermore, it was found that this lack of $Ca^{2+}$ influx rescued mitochondria depolarization and apoptosis.

In this regard, FIG. 3(F) shows the representative histograms overlay showing mitochondrial depolarization evaluated through TMRE measurement, 24 h after TDZ, EGTA or EGTA+ TDZ treatment and FIG. 3 (G) shows the cell death (Annexin V+, PI+ and Annexin V+/PI+) evaluated 24 h after TDZ, EGTA or EGTA+ TDZ treatment in t(6;11) SHI-1 and non-t(6;11) HL60, compared with DMSO value.

For these evidences, the Applicant concluded that this is the mechanism trough which TDZ induces t(6;11) AML to cell death.

Example 3—Comparison of TDZ with TDZ2 and TDZ6

The two compounds according to Example 1 (TDZ2) and Example 2 (TDZ6) were tested and compared with TDZ in vitro and in vivo, in terms of cytotoxicity on pediatric acute myeloid leukemia cells harboring the t(6;11)(q27;q23) KMT2A/AFDN rearrangement by means of apoptosis assay, and of occurrence of neuroleptic effects in vivo in mice by measuring akinesia through stepping test, as well as to to verify their mechanism of $Ca^{2+}$ influx.

Figure 4:
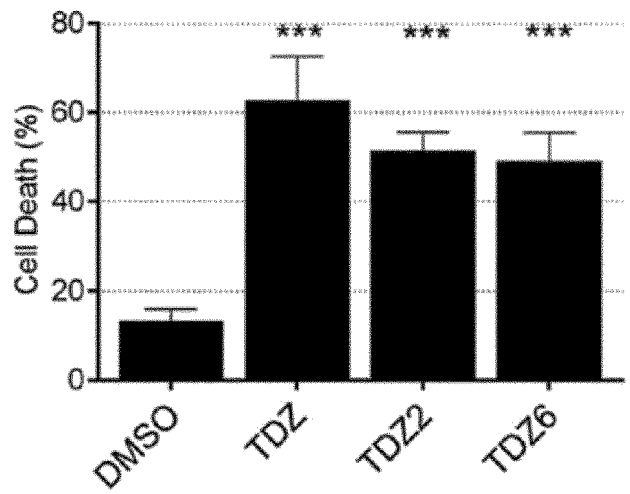
FIG. 4 shows a comparison of the apoptosis carried out with TDZ and with compounds according to Examples 1 (TDZ2) and 2 (TDZ6) in t(6;11) SHI-1 cell lines, live intracellular $Ca^{2+}$ measurement in SHI-1 cells loaded with Fluo-4 AM $Ca^{2+}$ indicator by flow cytometry, in $Ca^{2+}$-containing, or in $Ca^{2+}$-free buffer, and the stepping test performed after DMSO, TDZ, TDZ2 and TDZ6 i.p. injection in NSG mice. Data are presented as mean±SEM. *P<0.05; P<0.01; *P<0.001.
Figure 4:
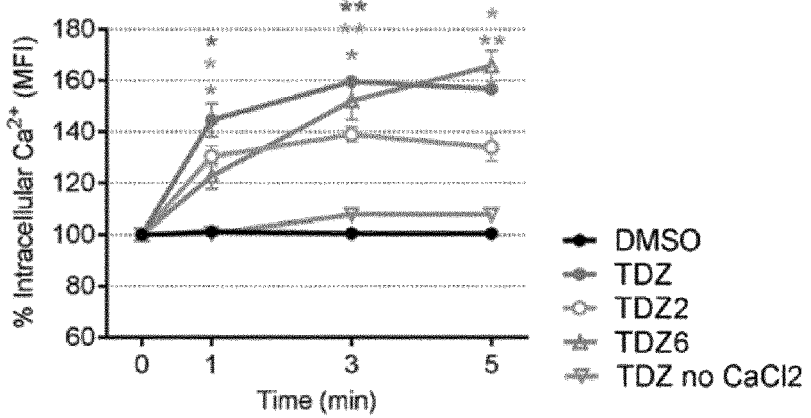
Figure 4:
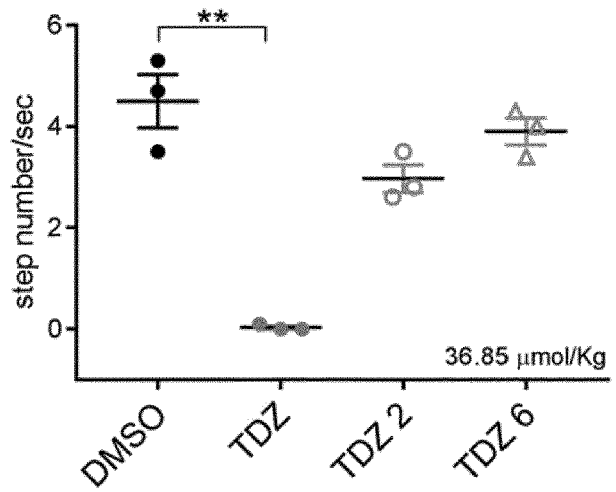

In this regard, FIG. 4 (A) shows the cell death (Annexin V+, PI+ and Annexin V+/PI+) induced by TDZ and the two analogues TDZ2 and TDZ6 in t(6;11) SHI-1 cell lines 24 h after treatment, FIG. 4 (B) shows the live intracellular $Ca^{2+}$ measurement in SHI-1 cells loaded with Fluo-4 AM $Ca^{2+}$ indicator by flow cytometry, in $Ca^{2+}$-containing, or in $Ca^{2+}$-free buffer, and FIG. 4 (C) shows the stepping test performed 1 h after DMSO, TDZ, TDZ2 or TDZ6 i.p. injection in NSG mice. Drugs were administered at 36.85 μmol/Kg, that is the corresponding dose of 15 mg/kg of TDZ.

The ability of TDZ2 and TDZ6 to maintain cytotoxic activity on t(6;11) AML cells both in vitro and in vivo was observed (FIG. 4 (A)), confirming also the same mechanism of $Ca^{2+}$ influx of TDZ (FIG. 4(B)). Importantly, it was noted that the TDZ analogues according to the invention, used at the molar dose corresponding to 15 mg/kg of TDZ, a concentration that provokes severe central side effects, did not induce neuroleptic effects in vivo in mice by measuring akinesia through the stepping test (FIG. 4 (C)), indicating that the TDZ analogues TDZ2 and TDZ6 according to the invention did not generate side effects on CNS, resulting safe for pediatric applications.

The invention claimed is:

1. A compound of formula (I):

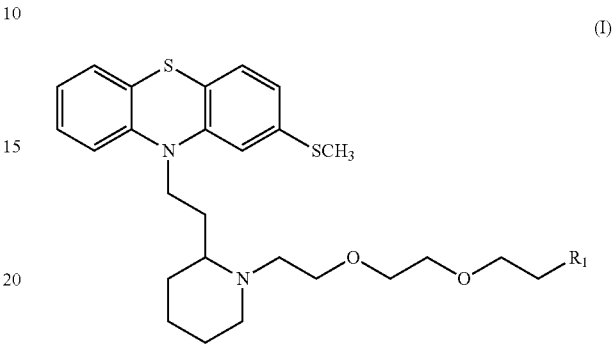

(I)

wherein R1 is $OCH_3$ or $NH_2$.

2. The compound according to claim 1, wherein R1 is $OCH_3$.

3. The compound according to claim 1, wherein R1 is $NH_2$.

4. A method for treating a tumor, which comprises administering to a patient in need thereof an effective amount of compound according to claim 1, wherein the tumor is acute myeloid leukemia.

5. The method according to claim 4, wherein the acute myeloid leukemia is pediatric acute myeloid leukemia harboring the t(6;11)(q27;q23) KMT2A/AFDN rearrangement.

* * * * *